(12) United States Patent
Kim et al.

(10) Patent No.: US 8,989,345 B2
(45) Date of Patent: Mar. 24, 2015

(54) METHOD FOR EVALUATION OF DENSITY PROFILE IN CARBON/CARBON MATERIAL AND METHOD FOR PRODUCTION OF STANDARD DENSITY TEST BLOCK USED THEREIN

(75) Inventors: Dong Ryun Kim, Daejeon (KR); Nam Gyun Yun, Daejeon (KR)

(73) Assignee: Agency for Defense Development, Daejeon (KR)

( * ) Notice: Subject to any disclaimer, the term of this patent is extended or adjusted under 35 U.S.C. 154(b) by 399 days.

(21) Appl. No.: 13/583,431

(22) PCT Filed: Jul. 12, 2010

(86) PCT No.: PCT/KR2010/004513
§ 371 (c)(1),
(2), (4) Date: Sep. 7, 2012

(87) PCT Pub. No.: WO2011/132820
PCT Pub. Date: Oct. 27, 2011

(65) Prior Publication Data
US 2013/0003917 A1 Jan. 3, 2013

(30) Foreign Application Priority Data

Apr. 22, 2010 (KR) .......................... 10-2010-0037552

(51) Int. Cl.
*G01N 23/06* (2006.01)
*G01N 23/083* (2006.01)
(Continued)

(52) U.S. Cl.
CPC ................ *G01N 23/046* (2013.01); *G01N 9/24* (2013.01); *G01N 2001/2893* (2013.01); *G01N 2223/3306* (2013.01); *G01N 2223/633* (2013.01); *G01N 2223/419* (2013.01)
USPC .................. 378/54; 378/56; 378/207

(58) Field of Classification Search
CPC ....... G01N 23/00; G01N 23/02; G01N 23/04; G01N 23/046; G01N 23/06; G01N 23/083; G01N 9/24
USPC .................. 378/50, 53, 54, 56, 207
See application file for complete search history.

(56) References Cited

U.S. PATENT DOCUMENTS 4,228,351 A * 10/1980 Snow et al. ...................... 378/54
4,233,507 A * 11/1980 Volz ................................. 378/18
(Continued)

OTHER PUBLICATIONS

International Search Report dated May 25, 2011 issued in PCT/KR2010/004513.

*Primary Examiner* — Jack Berman
(74) *Attorney, Agent, or Firm* — Scully, Scott, Murphy & Presser, P.C.

(57) ABSTRACT

Disclosed are a method for evaluating a local density profile in a carbon/carbon material and a method for producing a standard density test block capable of quantitatively evaluating the density profile in the carbon/carbon material, wherein the method for evaluating the density profile includes a first step of preparing a standard density test block to be inserted in the carbon/carbon material, wherein the standard density test block is produced by using the same type of material as the carbon/carbon material and thereafter inserted in the carbon/carbon material, a second step of radiating X-rays onto the carbon/carbon material having the standard density test block inserted so as to obtain and correct computed tomographic image, and a third step of measuring a physical density by use of a linear attenuation coefficient of the computed tomographic image, whereby the local density profile can accurately be evaluated by use of a nondestructive testing and additionally such method can be utilized as an excellent means for improving processes and ensuring quality.

13 Claims, 4 Drawing Sheets

(51) Int. Cl.
*G01N 9/24* (2006.01)
*G01N 23/04* (2006.01)
*G01N 1/28* (2006.01)

(56) References Cited

U.S. PATENT DOCUMENTS

| | | | |
|---|---|---|---|
| 4,571,491 A * | 2/1986 | Vinegar et al. | 378/207 |
| 4,613,754 A * | 9/1986 | Vinegar et al. | 378/207 |
| 4,782,502 A * | 11/1988 | Schulz | 378/18 |
| 4,873,707 A | 10/1989 | Robertson | |
| 5,247,559 A | 9/1993 | Ohtsuchi et al. | |
| 5,253,170 A | 10/1993 | Kanamori et al. | |
| 5,673,303 A | 9/1997 | Hangartner | |
| 5,774,520 A | 6/1998 | Bolotin | |
| 5,949,846 A | 9/1999 | Stein et al. | |
| 2004/0218728 A1 * | 11/2004 | Heismann | 378/207 |
| 2005/0123089 A1 | 6/2005 | Man | |
| 2013/0089186 A1 * | 4/2013 | Payne et al. | 378/207 |
| 2013/0202078 A1 * | 8/2013 | Lee | 378/10 |

* cited by examiner

METHOD FOR EVALUATION OF DENSITY PROFILE IN CARBON/CARBON MATERIAL AND METHOD FOR PRODUCTION OF STANDARD DENSITY TEST BLOCK USED THEREIN

TECHNICAL FIELD

The present invention relates to a method for producing a standard density test block capable of quantitatively evaluating the density profile of a carbon/carbon material by employing a nondestructive testing, and a method for computing physical density through a computed tomography.

BACKGROUND ART

Carbon/carbon material denotes a porous material having only carbon left therein due to cycles of carbonization and impregnation. The porous portions locally have a density difference. The combustion test results show an inconsistent erosion rate in spite of using carbon/carbon materials having similar densities with respect to an entire volume, which is caused directly due to the local density difference of the carbon/carbon materials.

The local density of the carbon/carbon material can be physically computed by cutting, dissection and the like, but such mechanisms come with destruction of the carbon/carbon material. Consequently, supplementary data is merely obtained at the beginning stage of developing the carbon/carbon materials. Furthermore, if densities of those physically destructed carbon/carbon materials are computed, excessive time and cost are required. To overcome such drawbacks, a nondestructive testing for evaluating density more quickly and accurately has been introduced.

Examples of the method for nondestructively evaluating density include an ultrasonic density measurement, a density measurement using x-ray radiography, a computed tomography and the like. However, even if adapting one of such techniques, it is difficult to quantitatively measure a physical density. Studies on the density measurement have actively been conducted beginning with a bone mineral density measurement for diagnosing osteoporosis patients in a medical industry field. Nevertheless, density measurement still relies on experiences of engineers and causes large deviation between engineers, and different results are derived by the same engineer.

The ultrasonic density measurement is a method for obtaining density by using variations of delivery speed of ultrasonic waves or modulus of elasticity depending on media. However, this method has a disadvantage of low reproducibility and accuracy.

There are many methods proposed for measuring bone mineral density using X-ray images, but the difference of X-ray attenuation cannot be obviously specified with only one X-ray image, thereby generating considerable measurement errors. To overcome this, a study has been conducted on a technique for measuring thickness of a medium and a density distribution thereof using a metal step-wedge having plural steps; however, such technique can merely provide qualitative analysis results for density other than quantitative results.

A technique of measuring the density variation and density distribution of bone tissues using annihilation radiation has been disclosed in Densitometer for Determining the Density Distribution and Variation of Density of an Object filed by Bolotin in U.S. patent application (U.S. Pat. No. 5,774,520) in 1998. A positron emission source Na-22 is present at the center of X-ray detectors. One detector is designed to directly detect 511-KeV annihilation radiation generated from Na-22 and another detector measures the density of a target object placed between the Na-22 and the another detector by virtue of reaction between the 511-KeV annihilation radiation and the object. This technique uses monochromatic gamma rays so as to have an advantage of non-occurrence of beam hardening and also does not measure scattered radiation so as to have an advantage of acquisition of clear tomographic images. However, the density difference has merely been discriminated by measuring linear attenuation coefficients of bones, fat, muscles and the like and no quantitative density value has been given. Also, the use of 511-KeV annihilation radiation has limitation to a transmission capability through an object and the use of radioactive isotope is always linked to the problem of the radioactive safety supervision.

An error-correction technique, which permits very accurate imaging of the contours of the bones in vivo by producing a standard test block corresponding to the density and shape to be measured, has been introduced in X-ray Tomography Phantoms, Method and System filed by Roberton in U.S. patent application (U.S. Pat. No. 4,873,707) in 1989. The shape correction has been realized by varying internal and external diameters of the standard test block, and an empty space is present within the standard test block to be filled with a material. Such use of the standard test block can be useful for fabrication of orthopedic prostheses with a specific bone structure and correction of the bone structure; however, no quantitative density value has been provided.

A technique of measuring geometrical width and density of an object to be imaged by using density contours measured with computed tomographic images has been developed. This technique is disclosed in Method and Apparatus for Evaluation of Structural Width Tomography filed by Hangarter in U.S. patent application (U.S. Pat. No. 5,673,303) in 1997. The existing tomography technique could not measure the accurate width and density with respect to a structure having a width below a minimum resolution value of image; however, this technique has measured the width of a specific structure, the width smaller than the minimum resolution value, by measuring a full width at half maximum (FWHM) based upon a maximum density value. The technique is capable of measuring thickness and density of cortex bones; however, the density measurement has been made simply by the sum of densities within the full width at half maximum, and thereby the qualitative results are merely provided.

The quantitative density profile of carbon/carbon material by employing a computing tomography has been disclosed in Density Profile Evaluation of Needle-punched Carbon/Carbon Composites Nozzle Throat by the Computed Tomography, introduced in the first paper, vol. 10, in the journal of the Korean Society of Propulsion Engineers Transaction in 2006. In this technique, for evaluating the density profiles, the density resolution test block and standard density test block has been measured so as to measure the density profile by using standard density materials of the standard density test block.

However, this technique has a disadvantage that the local density cannot directly be measured because the correlation between the density and the linear attenuation coefficient of different types of materials, such as distilled water, NaCl water solution, magnesium and PVDF, which are inserted in inner holes made of acryl, is different from the correlation between the density and the linear attenuation coefficient of a carbon group. To overcome such disadvantage, it has been assumed that the difference of the linear attenuation coefficients with respect to the distilled water and NaCl water solution obtained from the standard density test block is to be equally applied to the carbon/carbon material, and the entire density of the carbon/carbon material has been measured, followed by indirect measurement of the local density using the difference of the linear attenuation coefficients between the distilled water and the NaCl water solution. Thus, this technique must perform complicated processes of correcting each slice image to evaluate the local density.

In addition, the standard density test block produced in the technique uses the acryl-based material other than the carbon/carbon material, which disables a direct correction of beam hardening, resulting in a disadvantage of correcting and checking the beam hardening by using the cylindrical carbon/carbon material.

DISCLOSURE OF INVENTION

Technical Problem

An object of the present invention is to allow measurement of a local density of a carbon/carbon material without use of a destructive testing such as cutting and dissection, and more particularly, to provide a method for producing a standard density test block capable of quantitatively measuring the local density profile of the carbon/carbon material and computing the linear attenuation coefficient into physical density values.

Solution to Problem

To achieve the object or other advantage of the present invention, there is provided a method for evaluating a density profile in a carbon/carbon material, in a method for quantitatively measuring a density profile in a carbon/carbon material, the method including, a first step of preparing a standard density test block to be inserted in the carbon/carbon material, wherein the standard density test block is produced by using the same type of material as the carbon/carbon material and thereafter inserted in the carbon/carbon material, a second step of radiating X-rays onto the carbon/carbon material having the standard density test block inserted so as to obtain and correct computed tomographic image, and a third step of measuring a physical density by use of a linear attenuation coefficient of the computed tomographic image. The standard density material and the beam hardening correction material are made of a carbon-based material, the carbon-based material may include graphite.

The standard density test block may include a plurality of standard density materials each having a different density, and a beam hardening correction material having a plurality of internal holes, the plurality of standard density materials being inserted into the corresponding internal holes in a spaced state therebetween.

At least two of the plurality of standard density materials may be produced to constantly have a minimum density difference for allowing check of resolution.

Vacuum grease may be coated between the internal holes of the beam hardening correction material and the standard density materials for eliminating air spaces therebetween.

An outer appearance of the beam hardening correction material may be produced in a shape capable of being inserted in the carbon/carbon material, and vacuum grease may be coated between an outer surface of the correction material and inner wall surfaces of the holes of the carbon/carbon material for eliminating air spaces therebetween.

The second step may be configured to radiate the X-rays to the carbon/carbon material having the standard density test block inserted therein, to simultaneously measure the standard density test block and the carbon/carbon material.

The second step may further include correcting the beam hardening of the computed tomographic image using the beam hardening correction material.

The third step may be configured to derive the correlation between linear attenuation coefficient and density of each of the standard density materials and measure a linear attenuation coefficient of the carbon/carbon material at a preset position using the correlation between the linear attenuation coefficient and the density of each standard density material.

In accordance with one embodiment of the present invention, there is provided a method for producing a standard density test block to be inserted in a carbon/carbon material for quantitatively measuring a density profile of the carbon/carbon material through a computed tomography, and a standard density test block produced by the method, the method including producing a plurality of standard density materials by using the same type of material as the carbon/carbon material, the plurality of standard density materials each having a different density, producing a beam hardening correction material having a plurality of internal holes for inserting the plurality of standard density materials therein, the beam hardening correction material having a shape capable of filling an internal hole of the carbon/carbon material for inserting the standard density test block therein, so as to correct the beam hardening of X-rays passing through the carbon/carbon material, and coating a vacuum grease on the plurality of standard density material and inserting the same into the internal holes of the beam hardening correction material without air spaces therebetween.

Advantageous Effects of Invention

In accordance with the present invention, upon desiring to measure a local density profile of a carbon/carbon material using a computed tomography, the local density profile present within the carbon/carbon material can be accurately measured through a nondestructive testing.

A standard density test block produced in the present invention is made of the same type of material as the carbon/carbon material, so the correlation between a defined linear attenuation coefficient and the density can be directly used for evaluating a density at a preset position within the carbon/carbon material as the same type of material.

In accordance with one embodiment of the present invention, since the produced standard density test block can be measured together with the carbon/carbon material by executing a computed tomography, the correlation obtained from the standard density test block and the actual measurement of the carbon/carbon material can be achieved through a single tomographic image, thereby remarkably improving the measurement process and being widely utilized even in a product quality evaluation field.

MODE FOR THE INVENTION

Hereinafter, description will be given of a method for measuring the density profile of a carbon/carbon material in accordance with the preferred embodiment of the present invention, with reference to the accompanying drawings.

Figure 1:
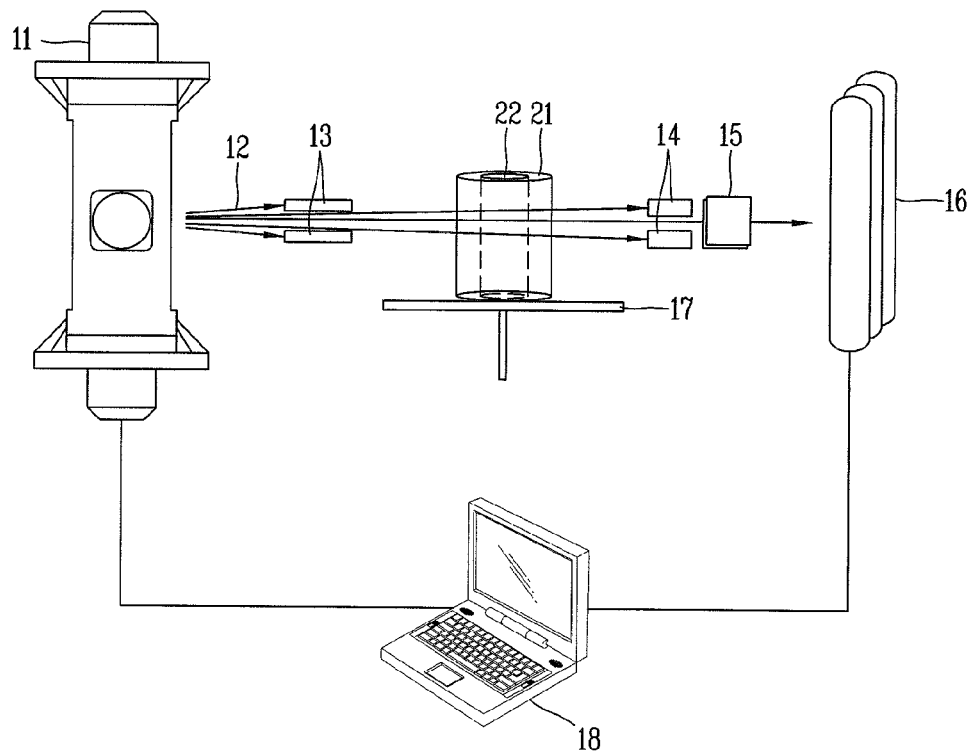
FIG. 1 is a schematic construction view of a density profile measurement system of a carbon/carbon material in accordance with the present invention.

FIG. 1 is a schematic construction view of a density profile measurement system of a carbon/carbon material in accordance with the present invention.

The density measurement system of the carbon/carbon material according to the present invention may include an X-ray radiation source 11 for generating X-rays, X-rays 12, a fan beam collimator 13, a slice thickness control lead shield 14, a dose control lead shield 15, an X-ray detector 16, a rotatable working table 17 and a controller or image processor 18.

The fan beam collimator 13 may be disposed in front of the X-ray radiation source 11. X-rays 12 generated by the X-ray radiation source 11 pass through the fan beam collimator 13, thereby minimizing the scattered X-rays and obtaining only fan X-rays required for a computed tomography.

The X-rays, which have passed through the fan beam collimator 13, are allowed to pass through a carbon/carbon material 21 and a standard density test block 22. The X-rays, which have passed through the carbon/carbon material 21 and the standard density test block 22, come with energy variation responsive to a linear attenuation coefficient belonging to each material.

Such X-rays, which have passed through the carbon/carbon material 21 and the standard density test block 22, then sequentially pass through the slice thickness control lead shield 14 and the dose control lead shield 15. During the process, the X-rays are defined in size with only necessary portions, thereafter reaching the X-ray detector 16.

To acquire tomographic images, the rotatable working table 17 is conveyed in a horizontal direction after tomography and then rotates by a predetermined angle to repeat the tomography. The thusly measured X-ray information is converted into tomographic images by the controller or image processor 18 for output.

Figure 2:
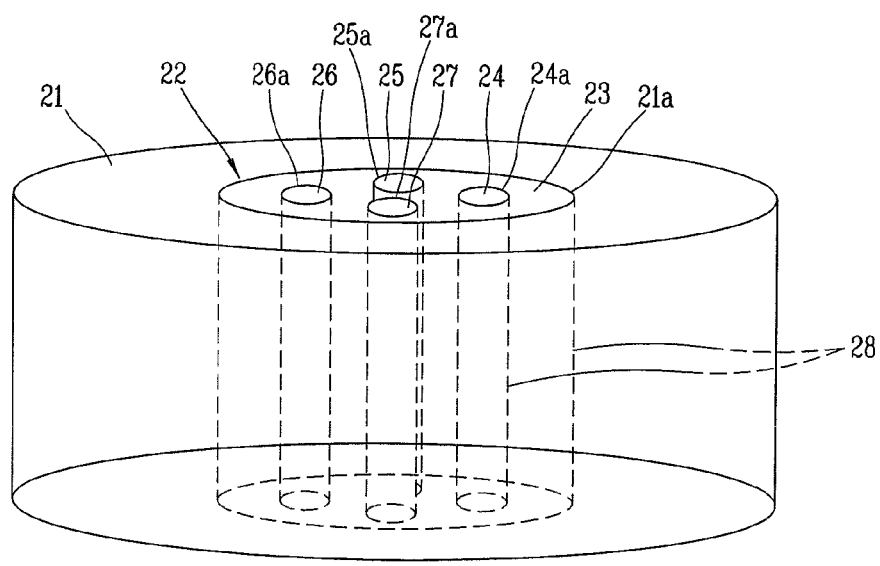
FIG. 2 is a perspective view illustrating a state where a standard density test block, produced for measuring (evaluating) the density profile of the carbon/carbon material, is inserted in the carbon/carbon material in accordance with the present invention.

FIG. 2 is a perspective view illustrating a state where a standard density test block, produced for measuring the density profile of the carbon/carbon material, is inserted in the carbon/carbon material in accordance with the present invention.

As illustrated in FIG. 2, the carbon/carbon material 21 to be measured may have a hole 21a at its central portion according to a shape (e.g., a nozzle throat), and the standard density test block 22 may be inserted into the hole 21a. The standard density test block 22 is produced to evaluate the correlation between linear attenuation coefficient and density, and may include a plurality of standard density materials 24, 25, 26 and 27 and a beam hardening correction material 23.

In the present invention, especially, the standard density test block 22 may be made of a carbon group, for example, graphite, namely, the same type of material as the carbon/carbon material 21. Accordingly, the evaluated correlation between the linear attenuation coefficient and the density of the standard density test block 22 can directly be used for evaluating density information using the measured linear attenuation coefficient corresponding to a specific position within the carbon/carbon material 21.

The standard density materials 24, 25, 26 and 27 are fabricated to evaluate the correlation between the linear attenuation coefficient and the density, and each of the standard density materials is fabricated by use of a material, such as a carbon-based graphite, having a different density value. The standard density materials 24, 25, 26 and 27, if possible, may be produced in a cylindrical shape so as to reduce noise, and at least two standard density materials may be arranged for obtaining the correlation. FIG. 2 illustrates four standard density materials 24, 25, 26 and 27 at a 90-degree interval. Two (e.g., 24, 25) of the standard density materials 24, 25, 26 and 27 may be produced to have a density difference of 0.01 $g/cm^3$ for evaluating density resolution.

The beam hardening correction material 23 may be produced to correct the phenomenon that when consecutive X-rays are transmitted through a medium, as the thickness of the medium increases, average energy of the X-rays increases, so as to lower the linear attenuation coefficient. Especially, the beam hardening correction material 23 is made of a carbon group, for example, graphite, having a uniform density.

The beam hardening correction material 23 may have an outer circumferential surface formed in a shape compliable with the hole 21a of the material 21 through an appropriate processing, and be provided therein with internal holes 24a, 25a, 26a and 27a for inserting the corresponding standard density materials 24, 25, 26 and 27 therein.

Prior to inserting the standard density materials 24, 25, 26 and 27 respectively in the internal holes 24a, 25a, 26a and 27a of the beam hardening correction material 23, a vacuum grease 28 may be coated on outer surfaces of the standard density materials 24, 25, 26 and 27 and inner wall surfaces of the internal holes 24a, 25a, 26a and 27a. The vacuum grease 28 is filled in gaps between the outer surfaces of the standard density materials 24, 25, 26 and 27 and the inner wall surfaces of the internal holes 24a, 25a, 26a and 27a, thereby eliminating air spaces, resulting in preventing the streak artifact from being generated on the computed tomographic image. Accordingly, it is preferable to minimize the gaps between the outer surfaces of the standard density materials 24, 25, 26 and 27 and the inner wall surfaces of the internal holes 24a, 25a, 26a and 27a. The vacuum grease 28 may also reduce a frictional force between the beam hardening correction material 23 and the standard density materials 24, 25, 26 and 27, which allows a smooth coupling between the standard density materials 24, 25, 26 and 27 and the beam hardening correction material 23.

When the standard density materials 24, 25, 26 and 27 are inserted into the beam hardening correction material 23, the vacuum grease may also preferably be coated on the outer circumferential surface of the beam hardening correction material 23 or an inner wall surface of the hole 21a of the material 21, so as to prevent the generation of the streak artifact on the computed tomographic image and achieve a smooth coupling.

Upon the insertion of the standard density test block 22 into the carbon/carbon material 21, the carbon/carbon material 21 and the standard density test block 22 undergo the computed tomography.

Figure 3:
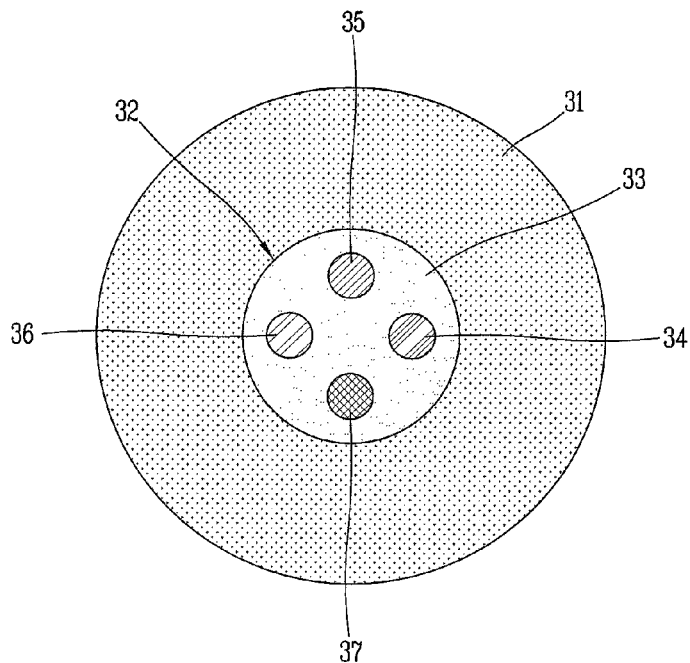
FIG. 3 is an exemplary view illustrating an image obtained by a computed tomography for the carbon/carbon material and a standard density test block assembly in accordance with the present invention.

FIG. 3 is an exemplary view illustrating an image obtained by the computed tomography for the carbon/carbon material and the standard density test block assembly in accordance with the present invention.

Referring to FIG. 3, the computed tomography of the carbon/carbon material according to the present invention is executed to simultaneously capture an image 31 of the carbon/carbon material 21 and an image 32 of the standard density test block 22. An image 33 of the beam hardening correction material 23 was used to correct the X-ray beam hardening. Images 34, 35, 36 and 37 of the standard density test block 22 each having a different density represent different linear attenuation coefficients on the computed tomographic image, and so indicated as different images.

Figure 4:
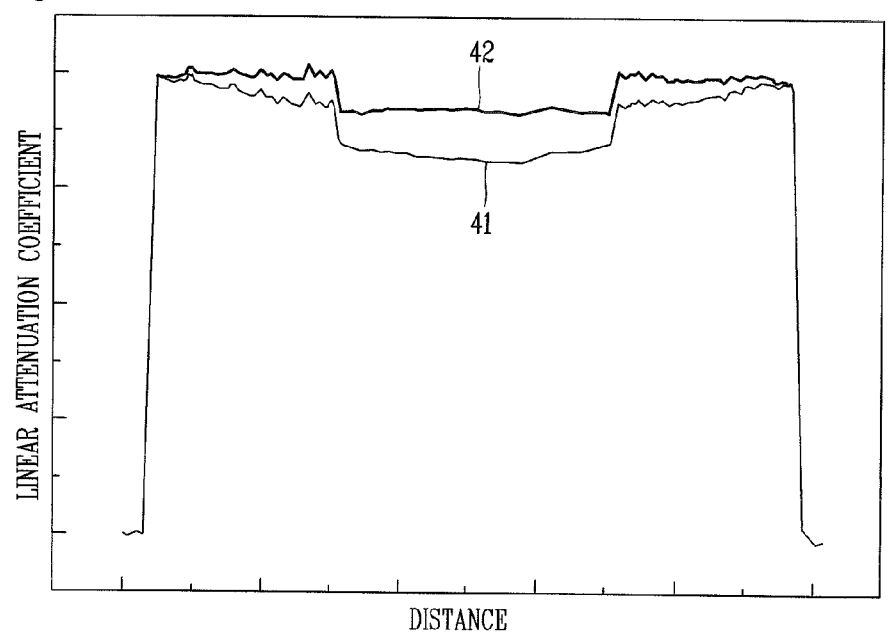
FIG. 4 is a graph illustrating a method for correcting beam hardening generated during the computed tomography of the carbon/carbon material applied to the present invention.

FIG. 4 is a graph illustrating a method for correcting beam hardening generated during the computed tomography of the carbon/carbon material applied to the present invention.

Concerning the beam hardening correction of the carbon/carbon material 21 according to the present invention, the computed tomographic image has been corrected by using the beam hardening correction material 23 of the standard density test block 22 and experimentally deciding beam hardening correction coefficients. Accordingly, it can be noticed that in the state of the same density, the linear attenuation coefficient 41 prior to the beam hardening correction was measured low at the central portion due to the shape of the material, whereas the linear attenuation coefficient 42 after the beam hardening correction was measured equal.

Figure 5:
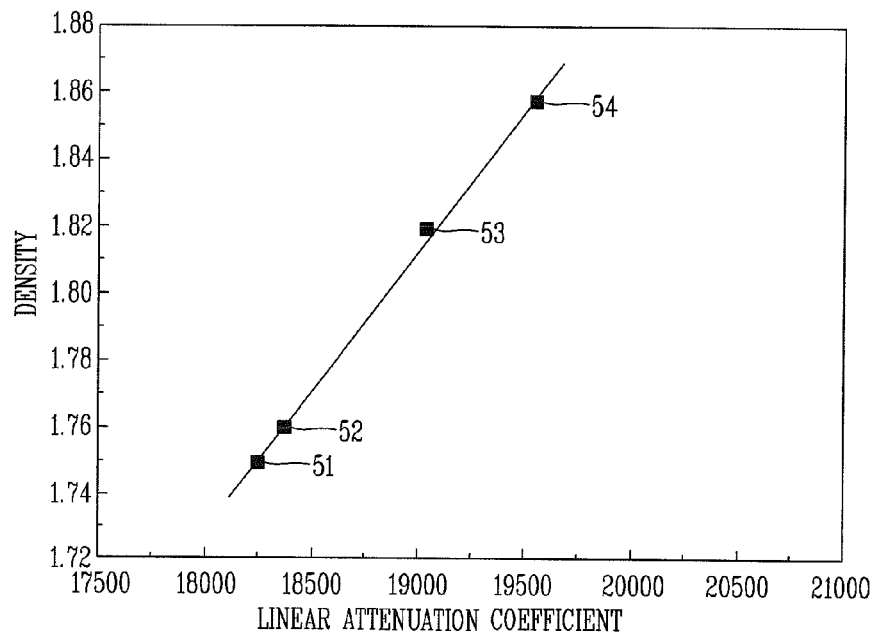
FIG. 5 is an exemplary graph illustrating a method for analyzing a correlation between linear attenuation coefficient and density of a standard density material based upon results obtained by the measurement system in accordance with the present invention.

FIG. 5 is an exemplary graph illustrating a method for analyzing a correlation between the linear attenuation coefficient and the density of a standard density material based upon results obtained by the measurement system in accordance with the present invention.

Prior to measuring the density profile of the carbon/carbon material 21, analysis should be first made for the correlation between linear attenuation coefficients of the standard density materials 24, 25, 26 and 27 obtained by the computed tomography and the densities of the standard density materials 24, 25, 26 and 27. That is, the already known densities of the standard density materials 24, 25, 26 and 27 may correspond to the linear attenuation coefficients measured from the standard density materials 24, 25, 26 and 27, respectively, so as to obtain the correlation therebetween. In detail, the first density of the first standard density material 24 and the first linear attenuation coefficient of the first standard density material 24 meet at the first position 51 on the graph, and the second density of the second standard density material 25 and the second linear attenuation coefficient of the second standard density material 25 meet at the second position 52. Similarly, the third standard density material 26 and the fourth standard density material 27 and corresponding densities meet at the third position 53 and the fourth position 54 on the graph, respectively. Such basic points (e.g., the first, second, third, fourth positions) are represented on the graph so as to finally obtain the linear correlation (i.e., line) between the density and the linear attenuation coefficient by a graph fitting. Here, it can be noticed that the first position 51 of the first standard density material 24 and the second position 52 of the second standard density material 25, the first and second standard density materials 24 and 25 being fabricated to have 0.01 g/cm³ density difference for evaluation of the density resolution, are sufficiently spaced apart from each other.

The measurement results of the standard density materials 24, 25, 26 and 27 simultaneously measured through the computed tomography and the thusly obtained correlation between the density and linear attenuation coefficient are directly used to measure the density profile of the carbon/carbon material 21. Such measurement method can simultaneously acquire facilitation and accuracy.

Figure 6:
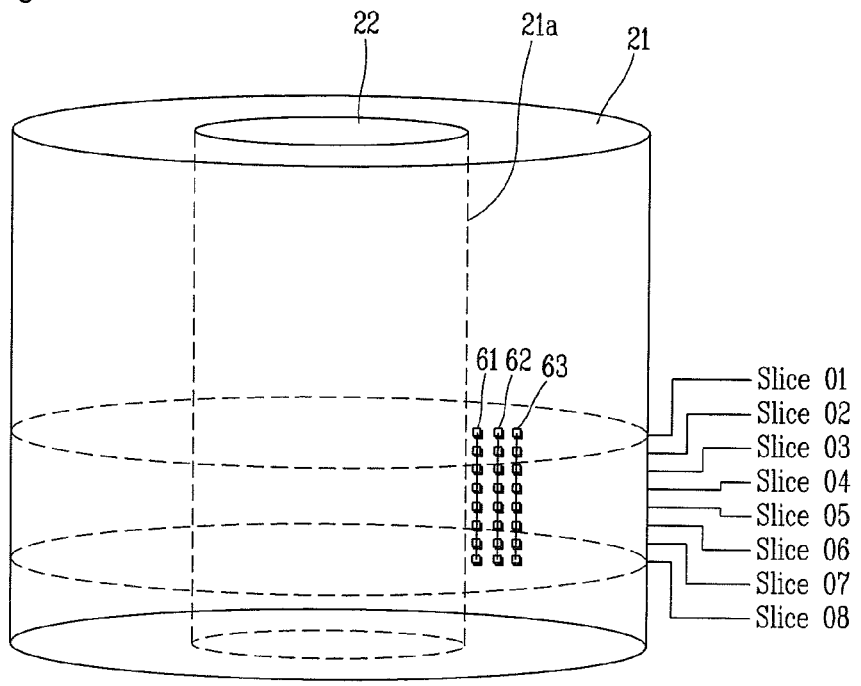
FIG. 6 is an exemplary view illustrating a method for acquiring the density profile depending on various measurement positions within the carbon/carbon material.

FIG. 6 is an exemplary view illustrating a method for acquiring the density profile depending on various measurement positions within carbon/carbon material.

The density profile of the carbon/carbon material according to the present invention has been measured at predefined positions, namely, a 5 mm-away position 61, a 10 mm-away position 62 and 15 mm-away position 63, based upon an inner wall surface of the hole 21a in a circumferential direction of the carbon/carbon material 21. Here, one measurement unit of a local density of the carbon/carbon material may be set to 2×2×1.5 mm. A local density obtained at one position may be set to correspond to voxel obtained from an image.

Similar to this, the measurement of the carbon/carbon material according to the present invention may be executed for a random position within the carbon/carbon material, and the measurement unit, namely, the size may be variable to a random size.

Figure 7:
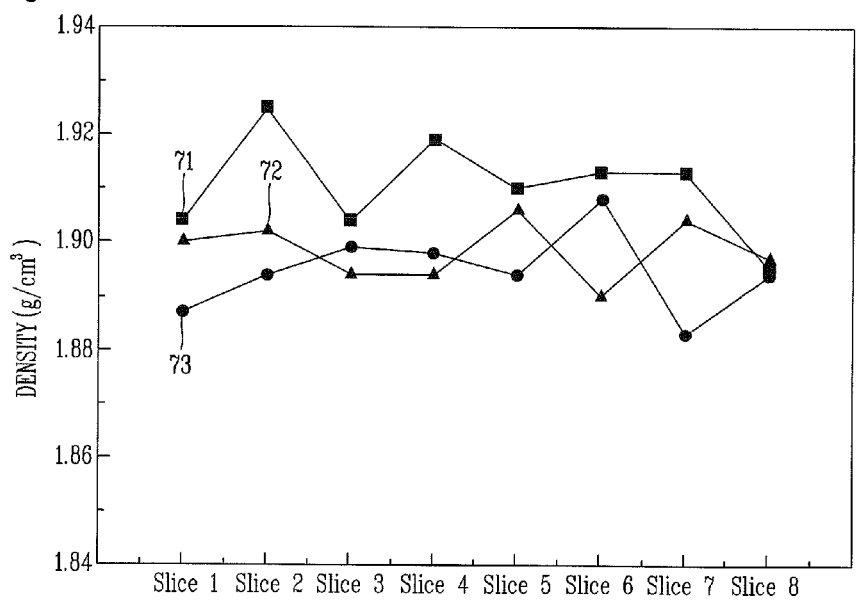
FIG. 7 is a graph illustrating the measurement results of the density profile of the carbon/carbon material at the measurement positions illustrated in FIG. 6.

FIG. 7 is a graph illustrating the measurement results of the density profile of the carbon/carbon material at the measurement positions illustrated in FIG. 6.

Regarding the density profile of the carbon/carbon material 21 according to the present invention, the 5 mm-away measurement position 61 from the inner diameter of the carbon/carbon material 21 corresponds to the first density profile 71, the 10 mm-away measurement position 62 from the inner diameter of the carbon/carbon material 21 corresponds to the second density profile 72, and the 15 mm-away measurement position from the inner diameter of the carbon/carbon material 21 corresponds to the third density profile 73. In addition, the density profiles from slide 01 to slice 08 are derived according to the distance.

When the measurement unit is 2×2×1.5 mm, the measured density is distributed within ±0.01 g/cm³ with 98.53% confidence, accordingly, the measurement error of the density profile of the carbon/carbon material according to the present invention may be negligible. Therefore, an accurate local density measurement can be advantageously ensured.

The aforesaid configuration and method for the method for measuring the density profile of the carbon/carbon material and the method for producing the standard density test block is not to be construed as limiting the present disclosure. This description is intended to be illustrative, and not to limit the scope of the claims. Many alternatives, modifications, and variations will be apparent to those skilled in the art. The features, structures, methods, and other characteristics of the exemplary embodiments described herein may be combined partially or entirely to obtain additional and/or alternative exemplary embodiments.

As the present features may be embodied in several forms without departing from the characteristics thereof, it should also be understood that the above-described embodiments are not limited by any of the details of the foregoing description, unless otherwise specified, but rather should be construed broadly within its scope as defined in the appended claims, and therefore all changes and modifications that fall within the metes and bounds of the claims, or equivalents of such metes and bounds are therefore intended to be embraced by the appended claims.

The invention claimed is:

1. A method for evaluating a density profile in a carbon/carbon material, in a method for quantitatively measuring a density profile in a carbon/carbon material, the method comprising:
   a first step of preparing a standard density test block to be inserted in the carbon/carbon material, wherein the standard density test block is produced by using the same type of material as the carbon/carbon material and thereafter inserted in the carbon/carbon material;
   a second step of radiating X-rays onto the carbon/carbon material having the standard density test block inserted so as to obtain and correct computed tomographic image; and
   a third step of measuring a physical density by use of a linear attenuation coefficient of the computed tomographic image.

2. The method of claim 1, wherein the standard density test block comprises:
   a plurality of standard density materials each having a different density; and
   a beam hardening correction material having a plurality of internal holes, the plurality of standard density materials being inserted into the corresponding internal holes in a spaced state therebetween.

3. The method of claim 2, wherein the standard density material and the beam hardening correction material are made of a carbon-based material, such as graphite.

4. The method of claim 2, wherein at least two of the plurality of standard density materials are produced to constantly have a minimum density difference for allowing check of resolution.

5. The method of claim 2, wherein the first step is configured to coat a vacuum grease between the internal holes of the beam hardening correction material and the standard density materials for eliminating air spaces therebetween.

6. The method of claim 2, wherein the first step is configured to produce an outer appearance of the beam hardening correction material in a shape capable of being inserted in the carbon/carbon material, a vacuum grease being coated between an outer surface of the correction material and inner wall surfaces of the holes of the carbon/carbon material for eliminating air spaces therebetween.

7. The method of claim 1, wherein the second step is configured to radiate the X-rays to the carbon/carbon material having the standard density test block inserted therein, to simultaneously measure the standard density test block and the carbon/carbon material.

8. The method of claim 7, wherein the second step further comprises correcting the beam hardening of the computed tomographic image using the beam hardening correction material.

9. The method of claim 1, wherein the third step is configured to derive the correlation between linear attenuation coefficient and density of each of the standard density materials and measure a linear attenuation coefficient of the carbon/carbon material at a preset position using the correlation between the linear attenuation coefficient and the density of each standard density material.

10. A method for producing a standard density test block, in a method for producing a standard density test block to be inserted in a carbon/carbon material for quantitatively measuring a density profile of the carbon/carbon material through a computed tomography, the method comprising:
    producing a plurality of standard density materials by using the same type of material as the carbon/carbon material, the plurality of standard density materials each having a different density;
    producing a beam hardening correction material having a plurality of internal holes for inserting the plurality of standard density materials therein, the beam hardening correction material having a shape capable of filling an internal hole of the carbon/carbon material for inserting the standard density test block therein, so as to correct the beam hardening of X-rays passing through the carbon/carbon material; and
    coating vacuum grease on the plurality of standard density material and inserting the same into the internal holes of the beam hardening correction material without air spaces therebetween.

11. The method of claim 10, wherein the standard density material and the beam hardening correction material are made of a carbon-based material, the carbon-based material comprising graphite.

12. The method of claim 10, wherein at least two of the plurality of standard density materials are produced to constantly have a minimum density difference for allowing check of resolution.

13. A standard density test block, in a standard density test block to be inserted in a carbon/carbon material for quantitatively measuring a density profile of the carbon/carbon material through a computed tomography, the test block comprising:
    a plurality of standard density materials made of the same type of material as the carbon/carbon material and each having a different density; and
    a beam hardening correction material having a plurality of internal holes for inserting the plurality of standard density materials, respectively, the beam hardening correction material having a shape capable of filling an internal hole of the carbon/carbon material for inserting the standard density test block therein, so as to correct the beam hardening of X-rays passing through the carbon/carbon material, wherein the plurality of standard density materials are respectively inserted in the beam hardening correction material in a vacuum grease-coated state without air spaces therebetween.

* * * * *